United States Patent
McFadden (10) Patent No.: US 7,628,561 B2
(45) Date of Patent: Dec. 8, 2009

(54) HEAD CLAMP RELEASABLE LOCKING DEVICE

(76) Inventor: Joseph T. McFadden, 513 Mowbray Arch, Suite 1400, Norfolk, VA (US) 23507-2134

( * ) Notice: Subject to any disclaimer, the term of this patent is extended or adjusted under 35 U.S.C. 154(b) by 353 days.

(21) Appl. No.: 11/358,141

(22) Filed: Feb. 22, 2006

(65) Prior Publication Data
US 2006/0185092 A1 Aug. 24, 2006

(51) Int. Cl.
*F16B 7/10* (2006.01)
*F16C 11/00* (2006.01)

(52) U.S. Cl. .................... 403/53; 403/110; 248/118; 5/637

(58) Field of Classification Search .............. 403/24, 403/53, 54, 55, 62, 63, 83, 84, 110, 180, 403/182, 300, 302, 321, 322, 324; 248/118, 248/118.1, 118.5, 278.1, 279.1, 287.1; 5/621, 5/622, 636, 637, 658; 606/54
See application file for complete search history.

(56) References Cited

U.S. PATENT DOCUMENTS

| | | | | |
|---|---|---|---|---|
| 289,180 A | * | 11/1883 | Tregurha | 248/279.1 |
| 3,099,441 A | * | 7/1963 | Ries | 5/637 |
| 4,108,426 A | * | 8/1978 | Lindstroem et al. | 5/637 |
| 4,169,478 A | * | 10/1979 | Hickmann | 606/151 |
| 4,545,572 A | * | 10/1985 | Day | 5/637 |
| 4,964,748 A | * | 10/1990 | McFadden | 403/55 |
| 5,254,079 A | * | 10/1993 | Agbodoe et al. | 602/32 |
| 5,269,031 A | * | 12/1993 | Alexander | 5/616 |
| 5,279,927 A | * | 1/1994 | Walls et al. | 430/331 |
| 5,560,728 A | * | 10/1996 | McFadden | 403/53 |
| 6,584,630 B1 | * | 7/2003 | Dinkler | 5/622 |
| 6,629,982 B2 | * | 10/2003 | Day et al. | 606/130 |
| 6,813,788 B2 | * | 11/2004 | Dinkler et al. | 5/622 |
| 7,117,551 B1 | * | 10/2006 | Dinkler et al. | 5/637 |
| 7,229,451 B2 | * | 6/2007 | Day et al. | 606/130 |
| 7,296,804 B2 | * | 11/2007 | Lechot et al. | 279/75 |
| 2006/0088370 A1 | | 4/2006 | McFadden | |

* cited by examiner

*Primary Examiner*—Michael P. Ferguson
*Assistant Examiner*—Nahid Amiri
(74) *Attorney, Agent, or Firm*—Jeffrey S. Melcher; Manelli Denison & Selter PLLC (57) ABSTRACT

A device for positioning and locking a head clamp in a selective position including a first arm, a second arm and a third arm. The third arm having a free end including both a spherical member carried in a socket and including a mounting tube and a gripping device to restrain movement of said spherical member. The head clamp includes a mounting post for insertion to said mounting tube wherein said mounting tube includes a releasable locking device for engaging and holding said mounting post against rotation and withdrawal of said mounting tube to prevent accidental release of the mounting post.

4 Claims, 7 Drawing Sheets

HEAD CLAMP RELEASABLE LOCKING DEVICE

FIELD OF THE INVENTION

The present invention is an improvement in the apparatus disclosed in my prior U.S. Pat. Nos. 4,964,748 and 5,560,728, both of which are incorporated herein by reference. Each of these patents relate to articulated arms and locking devices for a surgical head clamp such as is used in neurosurgery.

BACKGROUND OF THE INVENTION

As described in above noted prior U.S. patents, with the use of head clamps for positioning a patient's head for neurosurgery or other cranial surgery, it is necessary to provide a rigid support for the head and one which can be easily adjusted to allow access by the surgeon to selected portions of the head of the patient during an operation. To this end, my prior structures have provided three articulated arms each with locking levers so that once the head of a patient has been placed in a position as desired by the surgeon, the head can be locked in place. With my structure, selecting any position in space is a continuously variable, analog function. Also, during surgical operations, it is important that the stability and rigidity of the head supporting structure be assured once the position selection has been made. In the past, use of a number of types of head support structures has proven inadequate in terms of the possibility of accidental release of the support structure during a medical procedure. While the locking mechanisms of my prior patents noted above have lessened this possibility, there is a need for a head bracket support that will achieve rapid and secure locking of the head bracket in place without the possibility of rotation of the bracket relative to its support or release of the bracket.

SUMMARY OF THE INVENTION

The present invention provides an improvement in my prior devices that is easily accomplished yet inexpensive to install and which will positively prevent accidental release of the cranial bracket once placed in position for an operation. In a preferred embodiment, the head bracket is modified in that a single post is integrally formed with or attached to a portion of the bracket with the end of the post provided with recesses for cooperating with a holding device which will grip and lock the post against release as well as rotation once the post is inserted. With this arrangement, a quick release is also provided but one which requires a user to grab both the holding device for the post of the bracket as well as the bracket itself to effect release. Thus, accidental release will be discouraged if not positively prevented in all circumstances.

BRIEF DESCRIPTION OF THE DRAWINGS

The foregoing and further advantages of the present invention will become apparent as consideration is given to the following description taken in conjunction with the accompanying drawings, in which.

DETAILED DESCRIPTION

Figure 1A:
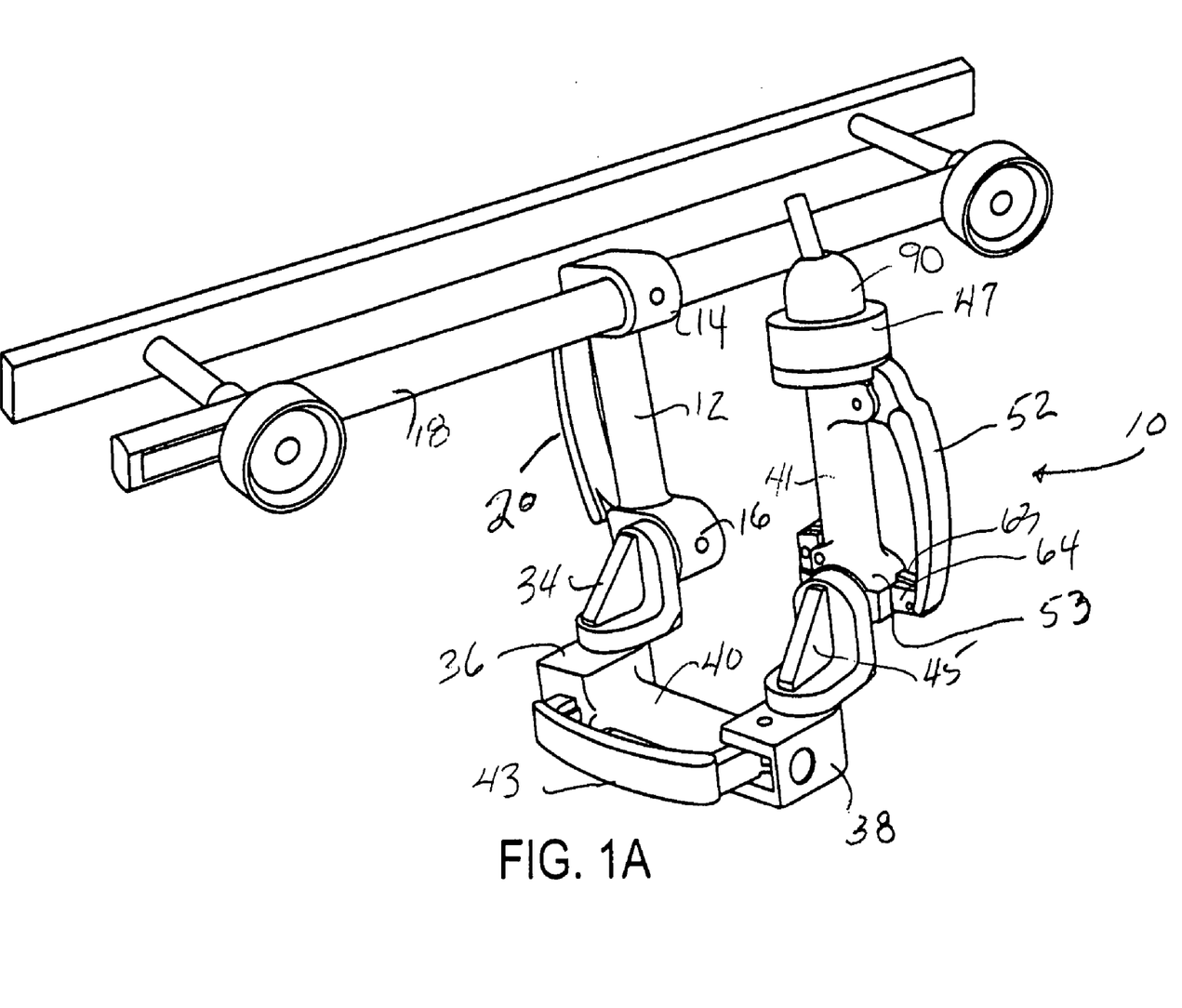
FIG. 1A is a perspective illustration of the articulated arms of present head clamp support structure which includes elements from my prior support structure.
Figure 2:
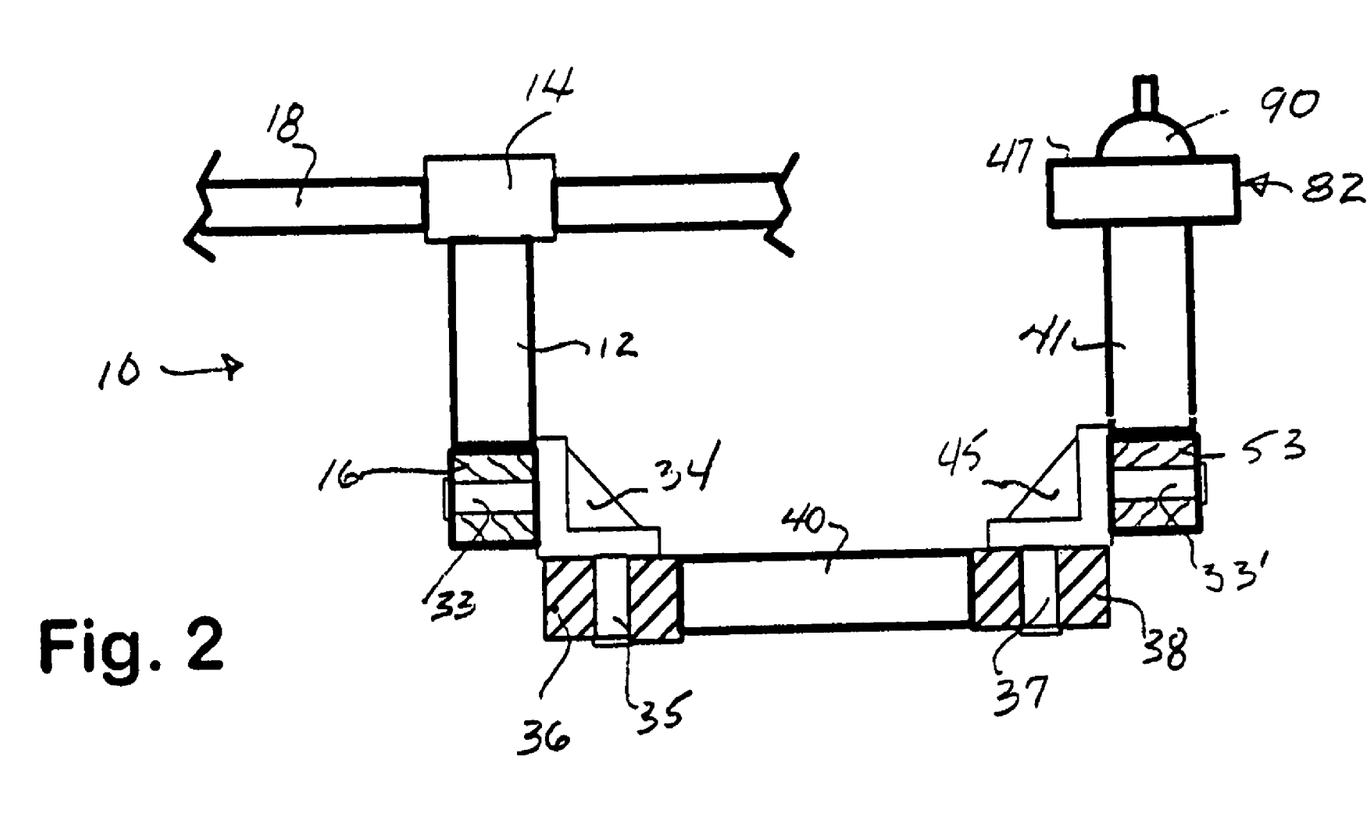
FIG. 2 is a side view, partly in section, of the device of FIG. 1 but with the arms rotated to another, selectable position and the levers deleted for clarity.

Referring to FIG. 1A, there is shown a view of a head positioning device similar to that of my prior U.S. Pat. No. 4,964,748, the disclosure of which is incorporated herein by reference. According to the present invention, the device 10 includes three arms 12, 40 and 41 with arm 12 being pivotally mounted on a rod 18 and held in position on the rod 18 by a clamping or gripping device 14 which is actuated by a locking lever 20. When tightened, the grip of the clamping device 14 on the rod 18 secures the arm 12 against rotation about rod 18 which itself will be attached to a rigid support such as a portion of the operating table. The opposite end of the arm 12 also has a similarly designed clamping device 16 which grips a pin 33 as shown in FIG. 2 which is connected to a bracket 34 from one face of which the pin 33 and from the other face of which a pin 35 projects. It will be apparent that the gripping action of the clamps 14 and 16 about their respective pivot members 18 and 33 will be substantially simultaneous upon closing of the lever 20. The same applies to the other arms 40 and 41 since the lever arm 43 activates gripping at both ends of the arm 40 while the lever arm 52 simultaneously activates the gripping device at 53 and the push lock device at 47 to secure locking device 90 in place. The gripping member 36 of the second arm 40 is adjustably positionable about pin 35 until its locking lever 43 (not shown in FIG. 2) is actuated to lock gripping members 36 and 38 on their respective pins 35 and 37, respectively. Pin 37 projects perpendicularly from one face of bracket 45 and another pin 33' projects from the other face of bracket 45 just as pin 33 projects from bracket 34. As shown in FIG. 1A, arm 41 is mounted at one end on the pin of bracket 45 while the free end 47 carries a locking device 90 which is described below.

Figure 1B:
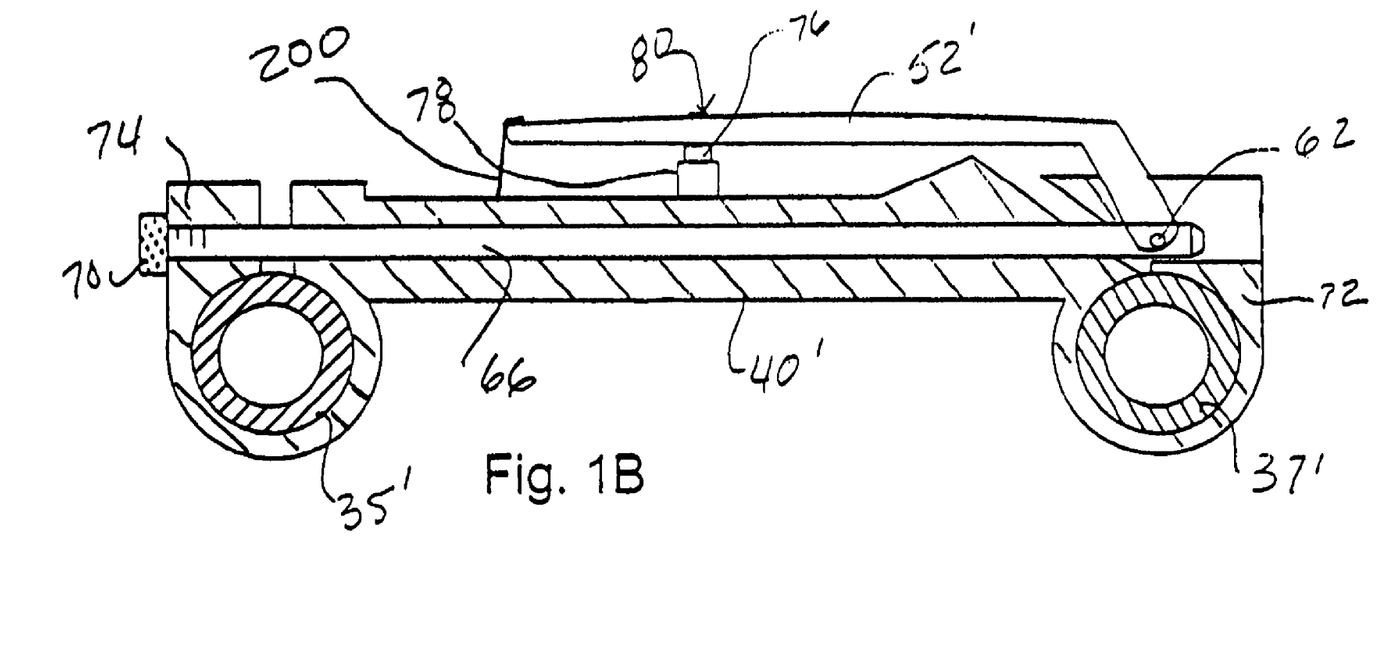
FIG. 1B is a side view in elevation, partly in section of a preferred version of the locking levers usable in the structure of FIG. 1A with a button operated locking device on the locking lever.

To ensure stability, the ends of lever arms 20, 43 and 52 will be provided with catch tabs 200, as shown in FIG. 1B which are arranged to receive a projection carried on the end of the levers opposite their pivotal attachment to their respective arms. The tongues 63, 64 will carry a spring biased ball detent to engage a recess on the projection of the respective arm to hold the arm in their locked positions. In a preferred form, the locking of the lever arms may be accomplished by the structure shown in FIG. 1B a variation of which is described in my co-pending application Ser. No. 10/941,944 which is incorporated herein by reference. In FIG. 1B, the locking lever 52' is pivotally mounted on a pin 62 extending between two walls, one of which is shown at 64, of a gap provided at the end of arm 40'. Also mounted on pin 62 is a rod 66 which extends through a bore formed in arm 40'. The opposite end of rod 66 is threaded to cooperate with an anchoring nut 70 which can be rotated to adjust the force exerted when the lever 52' is pivoted on pin 62 to bring the leg members 72 and 74 of arm 40' in gripping condition relative to the surfaces of pins 35' and 37'. The arm 40' is provided with a receiving cup 78 into which a shaft 76 can be inserted and which is provided with a detent arrangement, such as that described and shown in my copending application Ser. No. 10/941,944, so that once captured, release can only be effected by a conscious effort in pushing on the button 80 that extends through a bore in the lever 52'. Other types of arrangements to capture the locking lever arms will be apparent to those skilled in this art.

With reference to FIGS. 1A and 2, arm 41 is pivotable about a pin 33' similar to pin 33 but projecting perpendicularly from the face of the bracket 45 which is identical to bracket 34. Arm 41 can be locked in a position by actuation of the lever arm 52 (not shown in FIG. 2) and such actuation will lock gripping member 53 on the pin 33' of bracket 45 and at the same time will actuate the gripping function of locking device 90 at the free end of arm 41 as viewed in FIGS. 1A and 2 and which will now be described with reference to FIGS. 3A and 3B.

Figure 3A:
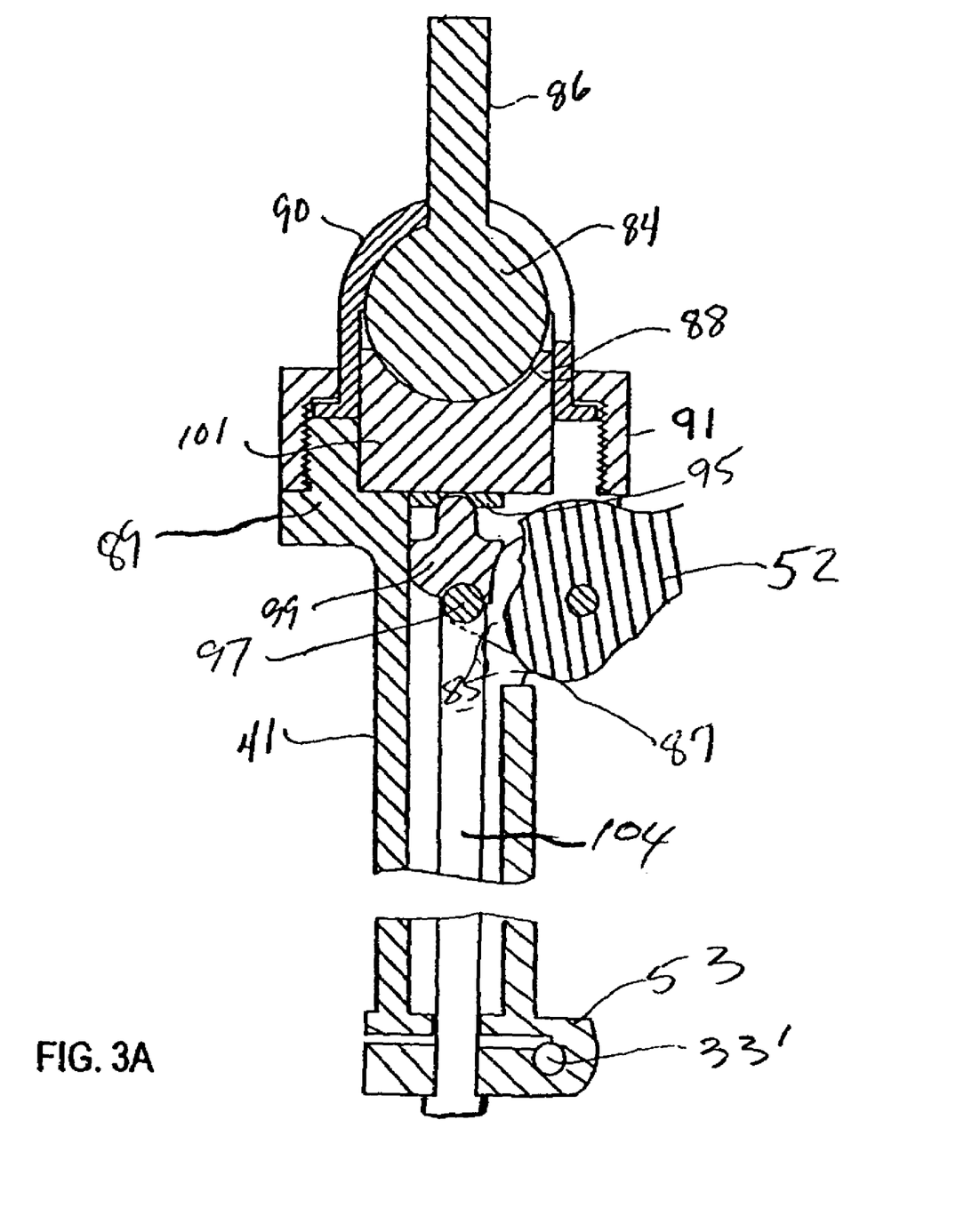
FIG. 3A is an enlarged, detailed view of the locking device of the present invention with parts broken away and with the post and ball as well as the clamping device in an unlocked condition.
Figure 3B:
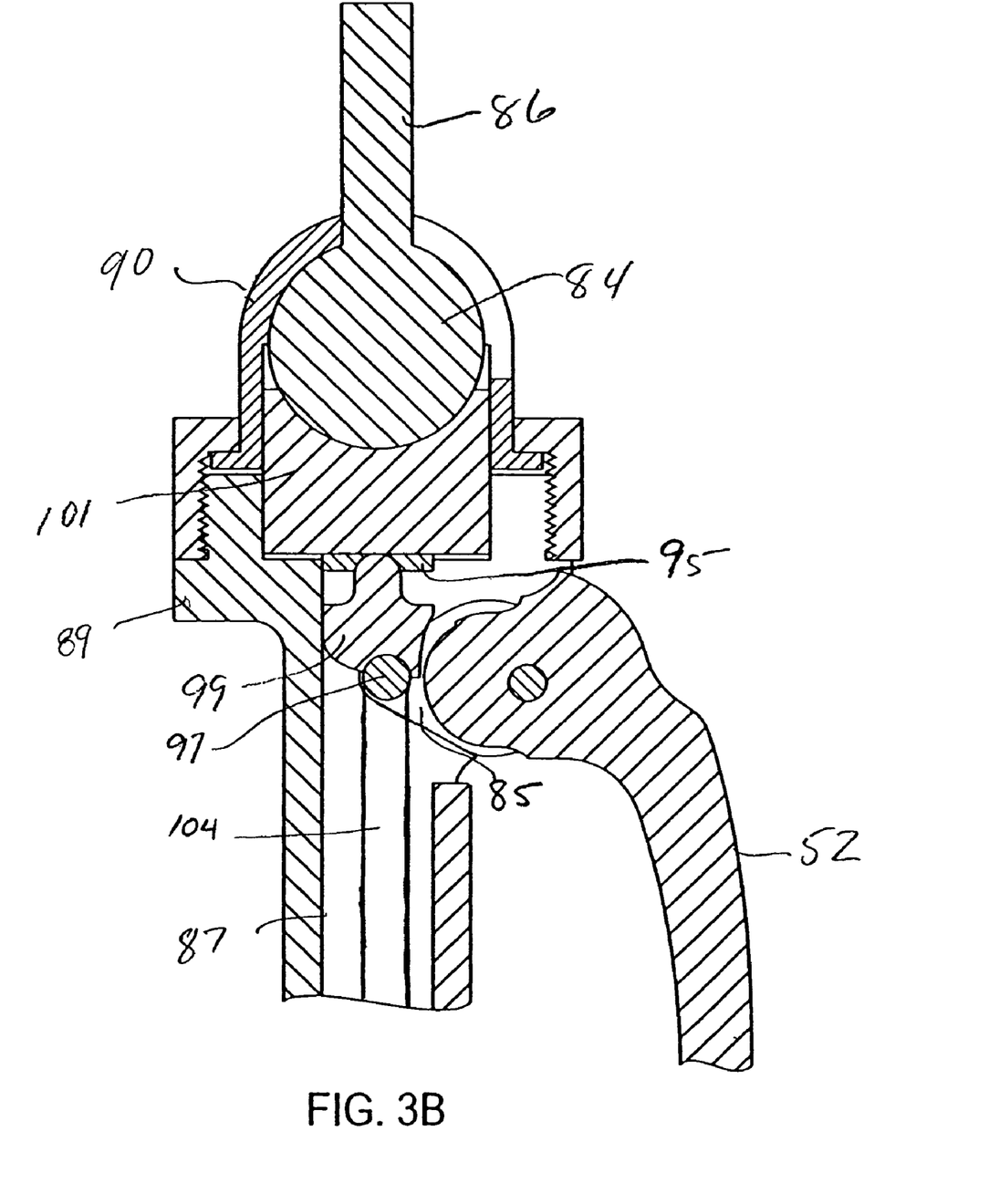
FIG. 3b is a view similar to FIG. 3A but with the post locking device in a locked condition.

The locking device 90 at the free end of arm 41 will operate to engage and hold the ball 84 from which post 86 extends and with which it is integrally formed. The post 86 is thus adjustably positionable in a socket 88 defined by the cover 91 which is rotatably carried on locking device 90 by the threaded housing 89 attached to body 91 formed on the end of arm 41. The post 86 is thus free to be positioned at any point relative to the axis of arm 41 through 360° of rotation about the axis of arm 41 and 180° of rotation about socket 88. A recess 87 is formed on the end of arm 41 to receive the toggle actuator 85 formed on the end of lever arm 52. An apertured plate 95 cooperates with toggle member 99 to move into or out of contact with the socket body to effect or release locking of the ball 84 in its housing. In FIG. 3A, the ball 84 is released while in FIG. 3B, the ball 84 is in its locked position. The shaft 104 operates in the same manner as shaft 66 described in conjunction with FIG. 1B in so far as the clamping device 53 is concerned so that the movement of the lever 52 will effect gripping of the pin 33' while at the same time moving toggle member 99 upwardly as viewed in this figure to lock the ball 84 in a selected orientation. To this end, the toggle actuator 85 includes a pin 97 which extends through the upper end of shaft 104. The opposite end of shaft 104 engages the gripping member 53 as shown.

Prior head brackets similar to head bracket 95 (FIG. 4) would include a hollow tube into which post 86 will be inserted and usually held by a threaded bolt provided in the tube to hold the post 92 in place. The bolt is tightened against the post 86 but any loosening of the threaded bolt will result in rotation of the bracket about the post 86 which is undesirable. In my co-pending U.S. application Ser. No. 10/941,944, a locking device for the levers and the unnumbered lever for the head bracket is provided. The present invention provides a secure mounting in place of the post 86 of a head bracket similar to the bracket shown in my U.S. Pat. No. 5,560,728 but where the head bracket is modified as shown in FIG. 4 to cooperate with the locking feature of FIG. 5.

Figure 4:
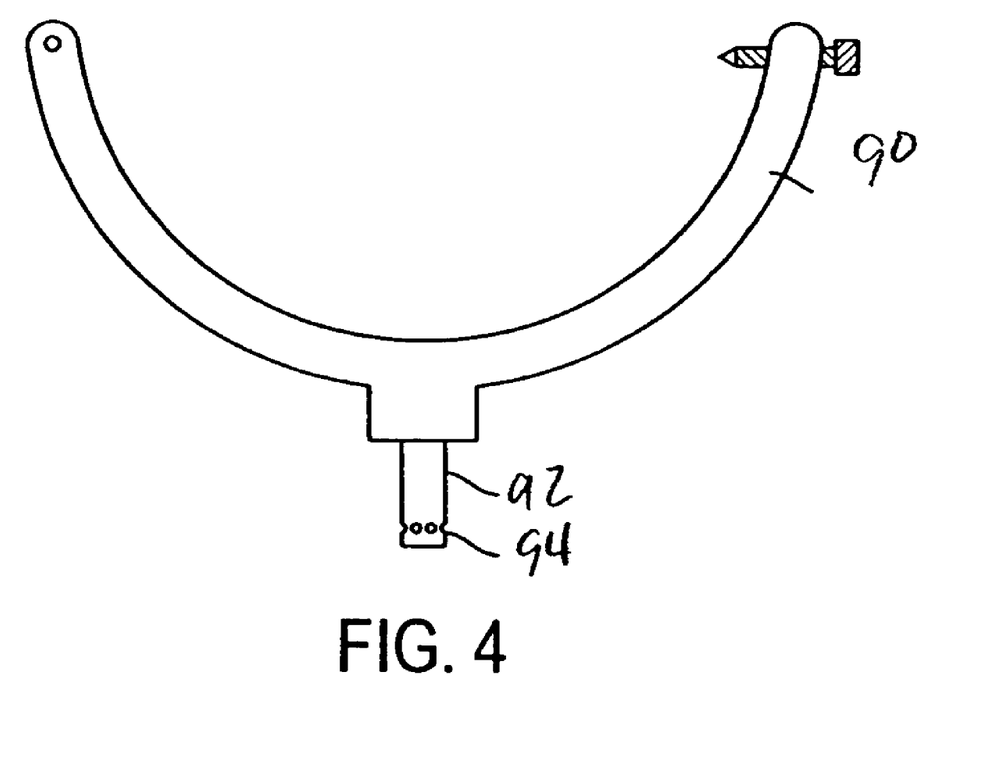
FIG. 4 is a plan view in elevation of a modified head bracket used in my present invention.
Figure 5:
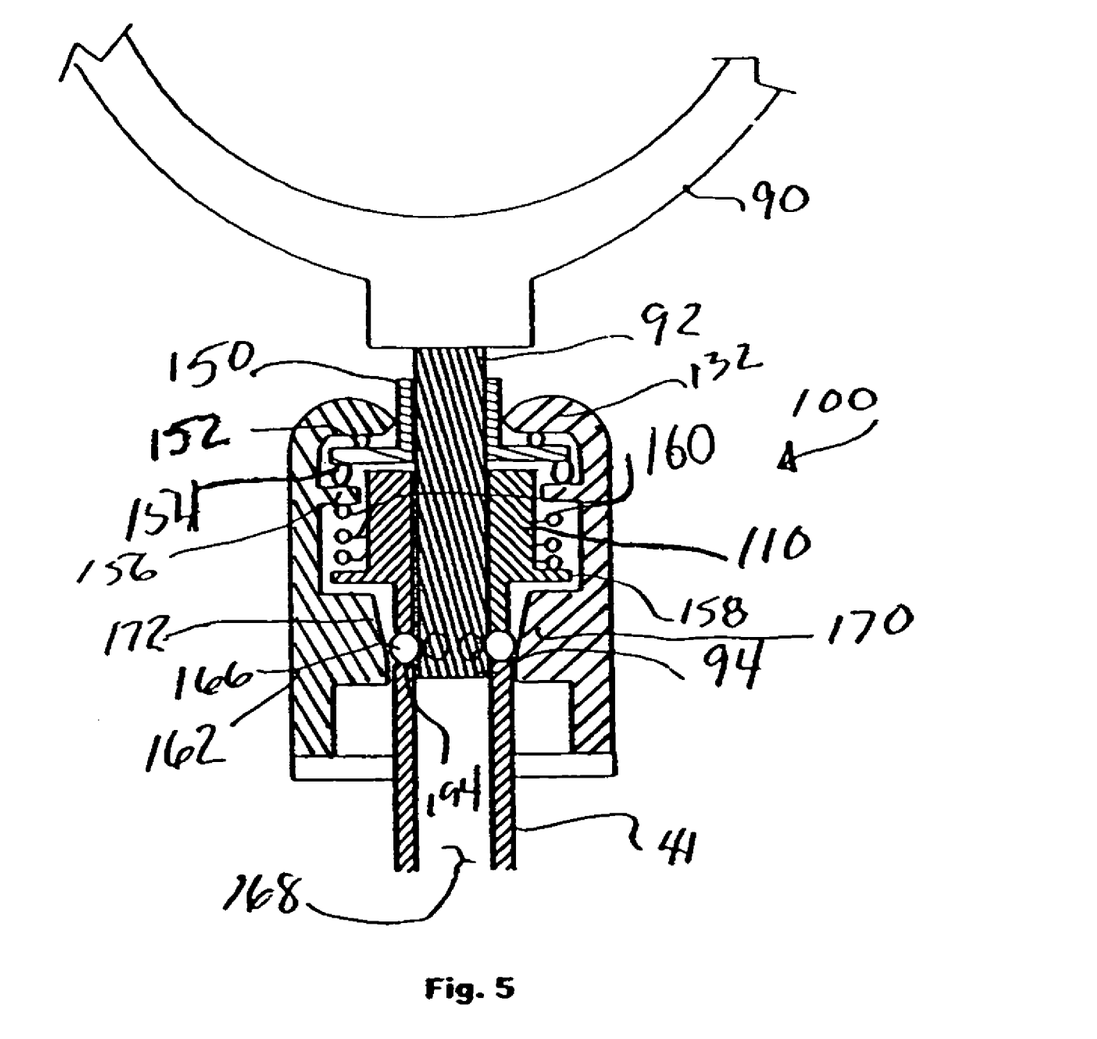
FIG. 5 is a detailed view, partly in section, of the locking device carried by a modified post and ball similar to the structures of FIGS. 3A and 3B.

As shown in FIG. 4, there is shown a conventional head bracket 95 where the mounting post 92 has been modified to include an annular array of spaced apart recesses 94 to cooperate with a holding device 100 as described below. The recesses 94 are preferably adjacent one end of the post 92. The device 100, as shown in FIG. 5, replaces the post 86 shown in FIGS. 3A and 3B on the end of arm 41. The arm 41, shown in FIG. 5, is provided at its end with a head 110 about which the locking device 100 is positioned and which carries a washer 150 rotatably supported between two seal rings 152 and 154. The locking device 100 is provided at one end with a peripheral flange 132 which extends radially inwardly toward the neck of the washer 150. The interior wall of the locking device 100 is provided with a radially inwardly extending flange 156 which supports the coil spring 160 on its upper side as shown in FIG. 5. The lower portion of the head 110 is also provided with a radially outwardly extending flange 158 which on its upper side supports one end of a coil spring 160 which acts between the flanges 156 and 158 to constantly urge the body 162 of the locking device 100 away from the arm 41 in an axial direction.

At a specific distance from the upper end of the arm 41, apertures 194 are formed in the wall of the arm 41 with each aperture carrying a detent ball 166. The apertures 194 will be shaped to limit the extent to which the individual balls may project into the interior 168 of the arm 41. Preferably, there are at least four apertures and corresponding balls and more preferably, six apertures and balls are used. As shown, the interior of the body 162 is formed with a radially inwardly projecting camming member 170 which has an annular, inner sloping cam surface 172 for engaging the balls 166. As viewed in FIG. 5, the lower portion of the surface 172 projects radially inwardly a greater extent than the upper sloping portion. With this arrangement, with the body 162 moved by the coil spring 160 away from the bracket 90 when the post 92 is inserted as shown, the balls are permitted to move away from the post 92. However, with the post 92 inserted and the body 162 moved downwardly by a user and then released, the lower portion of the camming surface 172 will urge the balls to each engage one of the recesses 94 formed adjacent the end of the post 92. This action will effectively lock the post 92 in device 100 as well as prevent relative rotation between the post 92 and the arm 41. Release of the post 92 and the bracket 90 is effected by a user grasping the bracket 90 and then moving the device 100 away from the bracket 90 to allow the upper portion of the camming surface 170 to move downwardly as viewed in FIG. 5 to allow the balls to be pushed back from their projecting position by the force applied by the movement of the post 92.

With this arrangement, it will be evident that accidental release of the post 92 is effectively prevented. It will also be apparent that the camming action of the locking device 100 may take a number of forms in addition to the one illustrated. For example, the locking function may be achieved by moving the camming surface axially away from the bracket 12 where the slope of member 70 is opposite to that shown. Another alternative may involve requiring relative movement between two annular members to position or change the position of the camming surface. Further, for increased resistance to accidental release, one can make the spring constant of spring 160 larger than conventional for surgical clamps.

Having described the invention, it will be apparent to workers in this field that various modifications can be made without departing from the spirit of this invention.

What is claimed is:

1. A device for positioning a surgical head clamp comprising a base and a plurality of arms, said plurality of arms each having a longitudinal axis and opposite ends, with a first arm being connected to the base, an intermediate second arm being connected between an end of said first arm and an end of a third arm with said arms connected so as to be pivotable about an end of the adjacent arm, at least one arm including a locking lever to lock the associated arm against pivoting relative to the adjacent arm, said third arm having a free end and including a spherical member carried in a socket and comprising an integrally formed mounting tube extending radially outwardly of said spherical member, said mounting tube being positionable at a selected point relative to the axis of said arm, said third arm including a gripping device to restrain movement of said spherical member in said socket, said device including a mounting post of a head clamp insertable into said mounting tube and having a plurality of recesses spaced about the surface of said post adjacent one end thereof, said mounting tube including a releasable locking device for engaging and holding said mounting post against rotation and withdrawal from said mounting tube so that accidental release of the mounting post is prevented, said third arm including a locking member for locking said spherical member against movement and for locking said third arm against pivoting movement relative to said second arm wherein said locking member is a lever pivotally carried adjacent the free end of said third arm and having an extension member extending through an opening in the end of said third arm to engage a toggle member which controls the locking of said spherical member in said socket.

2. A device as claimed in claim 1 wherein said releasable locking device includes a first body member having an interior and a through opening of a size to receive said mounting post, a second body disposed within said first body and being carried by the free end of said mounting tube, said second body including a plurality of openings in which detent balls are carried, said first body having a cam surface disposed to engage said detent balls when said first body is in a selected position relative to said second body, with said bodies being relatively movable against a spring element carried between said first and second bodies in order to release the mounting post of said head clamp from said mounting tube.

3. A device as claimed in claim 2 wherein the first body is movable parallel to the longitudinal axis of said mounting tube to effect release of said mounting post of said head clamp, said spring element operating to bring said cam surface away from said head clamp to thereby hold said detent balls in a locking position with said first body being movable away from said head clamp by a user to bring a portion of said cam surface to a position where said detent balls are in an unlocking position.

4. A device as claimed in claim 1 wherein said third arm includes a clamping shaft extending longitudinally through said third arm to engage and operate a clamping device at the opposite end of said third arm.

* * * * *

UNITED STATES PATENT AND TRADEMARK OFFICE
CERTIFICATE OF CORRECTION

PATENT NO.        : 7,628,561 B2                                            Page 1 of 1
APPLICATION NO.   : 11/358141
DATED             : December 8, 2009
INVENTOR(S)       : Joseph T. McFadden It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 635 days.

Signed and Sealed this

Second Day of November, 2010

David J. Kappos
*Director of the United States Patent and Trademark Office*